(12) United States Patent
Picha Muthu et al.

(10) Patent No.: US 8,709,036 B2
(45) Date of Patent: Apr. 29, 2014

(54) TENSION TRANSDUCING FORCEPS

(75) Inventors: Joseph Ezhil Rajan Picha Muthu, Pittsburgh, PA (US); Dinakar Golla, Pittsburgh, PA (US); David Alan Vorp, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 519 days.

(21) Appl. No.: 12/779,233

(22) Filed: May 13, 2010

(65) Prior Publication Data

US 2011/0009899 A1   Jan. 13, 2011

Related U.S. Application Data

(60) Provisional application No. 61/177,742, filed on May 13, 2009.

(51) Int. Cl.
*A61B 17/28* (2006.01)

(52) U.S. Cl.
USPC .............. 606/205; 606/207; 606/167; 606/51

(58) Field of Classification Search
USPC .................... 606/205–211, 51, 52, 167–170; 294/116
See application file for complete search history.

(56) References Cited

U.S. PATENT DOCUMENTS

| | | | | |
|---|---|---|---|---|
| 4,533,167 A | * | 8/1985 | Johnson | 294/86.4 |
| 5,209,747 A | | 5/1993 | Knoepfler | |
| 5,217,460 A | | 6/1993 | Knoepfler | |
| 5,339,799 A | * | 8/1994 | Kami et al. | 600/117 |
| 6,773,434 B2 | | 8/2004 | Ciarrocca | |
| 7,083,620 B2 | | 8/2006 | Jahns et al. | |
| 7,708,757 B2 | | 5/2010 | Ganter | |
| 2008/0147090 A1 | * | 6/2008 | Seibold et al. | 606/130 |
| 2010/0152586 A1 | * | 6/2010 | Grant et al. | 600/454 |
| 2010/0156127 A1 | * | 6/2010 | De Kervanoael | 294/106 |

FOREIGN PATENT DOCUMENTS

WO   WO 2009/000795   * 12/2008

OTHER PUBLICATIONS

Barnea et al., Delayed primary closure of fasciotomy wounds with Wisebands, a skin- and soft tissue-stretch device, Injury, International Journal of the Care of the Injured, 2006, 6 pages.
Bassini et al., Method for measuring suture tension in surgery, Medical & Biological Engineering & Computing, Jul. 1988, 451-454, vol. 26.
Chu et al., Nondestructive measurements of the properties of healing burn scars, Medical Instrumentation, May-Jun. 1975, 139-142, vol. 9 No. 3.
Jacquet et al., A new experimental method for measuring skin's natural tension, Skin Research and Technology, 2008, 1-7, vol. 14.
Ksander et al, Excisional Wound Biomechanics, Skin Tension Lines, and Elastic Contraction, Plastic & Reconstructive Surgery, Mar. 1977, 398-406, vol. 59 No. 3.
Tholey, Direct 3-D Force Measurement Capability in an Automated Laparoscopic Grasper, Eurohaptics, 2004.
Tholey et al., Design, Development, and Testing of an Automated Laparoscopic Grasper with a 3-D Force Measurement Capability, Medical Simulation: International Symposium, 2004, 38-48.

* cited by examiner

*Primary Examiner* — Gary Jackson
*Assistant Examiner* — Katrina Stransky
(74) *Attorney, Agent, or Firm* — The Webb Law Firm

(57) ABSTRACT

A forceps device is provided for performing a surgical procedure. The device comprises a closeable jaw comprising jaw members having one or more force sensors deployed in a manner to measure force applied to the jaws of the device.

17 Claims, 13 Drawing Sheets

TENSION TRANSDUCING FORCEPS

CROSS REFERENCE TO RELATED APPLICATIONS

This application claims the benefit under 35 U.S.C. §119 (e) to U.S. Provisional Patent Application No. 61/177,742, filed May 13, 2009, which is incorporated herein by reference in its entirety.

The aesthetic appearance and wound healing of surgical flaps depend on the tension applied to pull the distant tissues together for suturing and holding them in place. Unfortunately, the quantitative measurement of the tension is technically difficult due to a lack of reliable tension measuring device in a clinical setting. The need to maintain sterile conditions, ergonomic considerations, limited working space and the need for continuous data acquisition are other factors that have contributed to the lack of an ideal device. Study comparisons for various closure techniques as well as the selection and reliability of a suture for a given closure have been limited for the same reasons.

SUMMARY

A novel tension transducing forceps device is described herein. In its most general sense, the device comprises opposable jaws, one or both of the jaws comprise a force sensor for measuring force applied by each jaw. Each force sensor for each jaw is configured to measure force applied by the jaw.

DETAILED DESCRIPTION

Figure 1A:
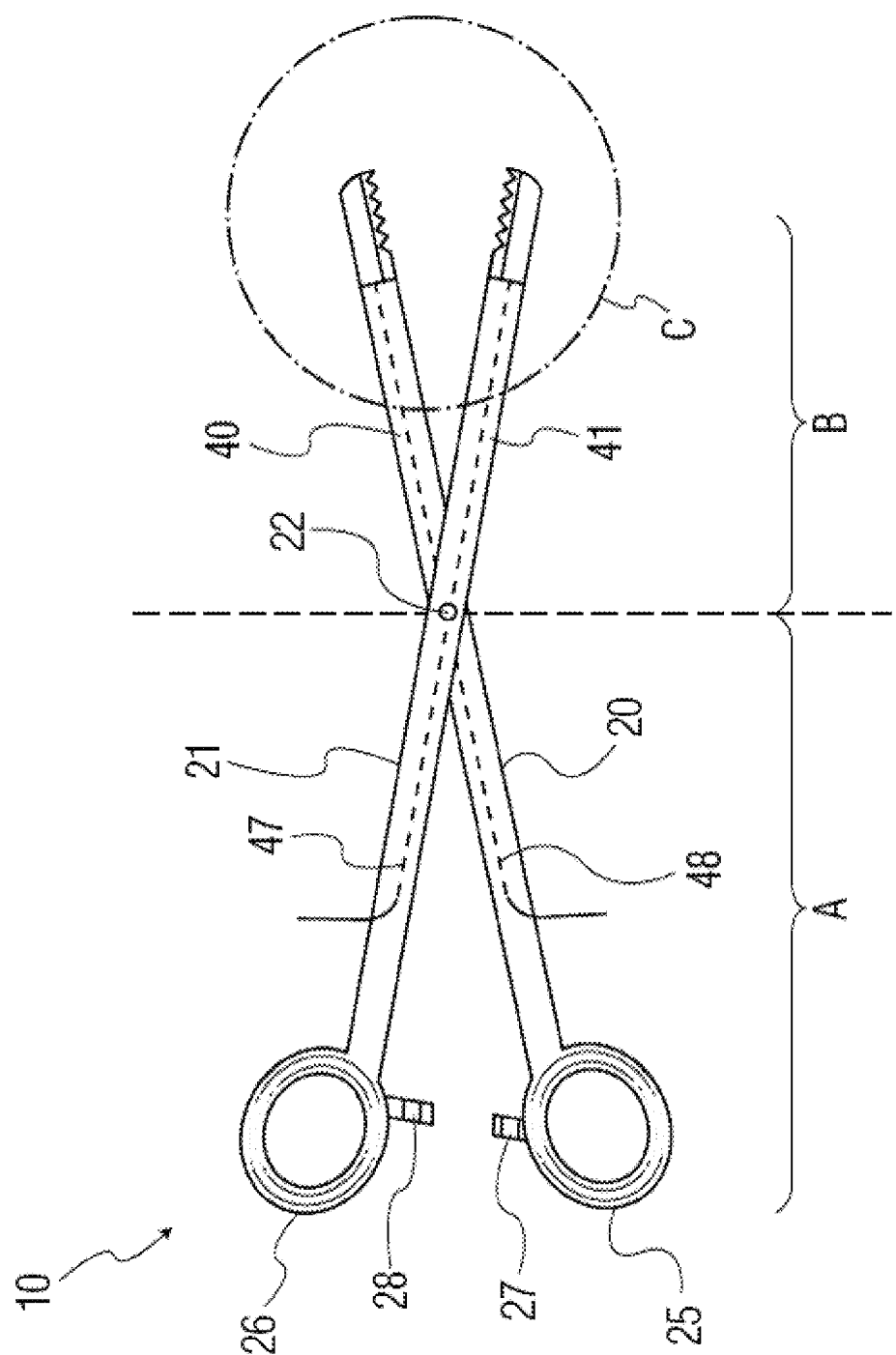
FIGS. 1A-D illustrate schematically various embodiments of a device described herein.

A device is provided that is useful, for example, for performing surgical procedures. The device comprises a closeable jaw and one or more force sensors in the closeable jaw for measuring forces applied by or to the jaw.

As used herein, the terms "comprising," "comprise" or "comprised," and variations thereof, are intended to be open-ended. Unless otherwise specified, the articles "a," "an," and "the" are used herein to refer to one or more than one.

In one embodiment, the device comprises jaw members each having inward-facing and outward-facing surfaces in which the inward-facing surfaces substantially face each other. The jaw members comprise distal gripping surfaces and one or both jaw members comprise an electronic force sensor configured to measure a force applied to the gripping surface. The device comprises a handle portion for holding, supporting, operating, etc. the device. The device also comprises a means for opening and/or closing the jaws, that is moving one or both of the jaws with respect to the other jaw. The device also comprises a conductor attached to each of the electronic force sensor(s) for conducting an electrical signal from the force sensor(s). Optionally, the conductor is attached to both a force sensor and an electrical circuit, electronic circuit, electronic device, PDA, or computer device that receives an electrical signal from the force sensor(s) and converts that signal into data output for storage and/or that can be detected by a human, such as on a display, printout, or a file computer process, such as a spreadsheet or database.

According to one embodiment, a device is provided comprising a jaw comprising jaw members pivotally attached to each other at a pivot axis. The jaw members comprising a gripping surface distal to the pivot axis. One or both, and in one example, both, jaw members comprise an electronic force sensor configured to measure a force applied to the gripping surface. The device also comprises levers mechanically linked to the jaws; and a conductor attached to the electronic force sensor.

As used herein, "distal" and "proximal" are directions referring to towards (proximal to) or away from (distal to) a typical user of the device. A scalpel has a proximal handle and a distal blade. A scissors has proximal handles and distal blades. Kelly forceps have proximal handles and a proximal locking mechanism and distal gripping jaws and distal gripping surfaces. The terms proximal and distal also can refer to the relative positioning of elements in a device. For example, in the context of Kelly forceps, the pivot axis is proximal to the gripping surface, but is distal to the loop handles.

As used herein a "lever" is a simple machine, meaning a rigid or substantially rigid member that is mechanically linked to the jaws so that the jaws can be moved by moving the lever. In a simple example, a scissors comprises two levers attached at a pivot axis to two blades that are integral with the levers. In the context of the device described herein, each jaw member is attached to a lever. One of the levers may be, in practice, immovable or is a part of a handle, guiding structure, such as a rod or wire, larger device or housing. For instance, in a catheter or arthroscopic device, one jaw member may be attached to a rod, handle or device housing, which is fixed, and the other jaw member is movable relative to the first jaw member.

As used herein in the context of the device, inward or inward-facing refers to towards a central point, line or plane of the device. For instance and inward-facing gripping surface on a jaw element faces substantially in a direction of a median line between jaw elements, and outward meaning substantially away from that line.

In one embodiment of the device, each lever comprising a shaft integral with each jaw members and extending from the pivot axis, such as is the case with a typical scissors or Kelly forceps.

In one embodiment, the jaw members each comprise inward-facing and outward-facing surfaces. This embodiment further comprises a force sensor on the outward facing surface of one or both of the jaw members. This embodiment also comprises an arm having a proximal and distal portion pivotally attached at a second pivot axis to a distal end of each jaw member comprising the force sensor, the distal portion of the arm extending beyond a distal portion of the jaw member and comprising the gripping surface on an inward-facing side of the arm, the proximal portion of the arm extending over the force sensor and which engages the electronic force sensor when force is applied to the an inward-facing side of the gripping surface causing the arm to pivot about the second pivot axis. In one embodiment, the arm is be pivotally attached to pivot or rotate in substantially the same plane as the movement of the jaw members.

In a similar embodiment, the jaw members each comprise inward-facing and outward-facing surfaces. However, this embodiment further comprises a force sensor on the inward-facing surface of one or both of the jaw members. This embodiment also comprises an arm having a proximal and distal portion pivotally attached at a second pivot axis to a distal end of each jaw member comprising the force sensor, the distal portion of the arm extending beyond a distal portion of the jaw member and comprising the gripping surface on an outward-facing side of the arm, the proximal portion of the arm extending over the force sensor and which engages the electronic force sensor when force is applied to the an outward-facing side of the gripping surface causing the arm to pivot about the second pivot axis. In one embodiment, the arm is be pivotally attached to pivot or rotate in substantially the same plane as the movement of the jaw members.

In any embodiment comprising the arm(s) pivotally attached to the jaw member(s), the proximal portion of the arm facing the electronic force sensor may comprise a protuberance aligned to engage the force sensor—that is, to engage the force sensor when force is applied to the gripping surface, pivoting the protuberance to press onto the force sensor. In any embodiment comprising the arm(s) pivotally attached to the jaw member(s), one of the arms or the shafts may comprise one or more stops for limiting movement of the arm about the pivot axis.

The force sensor may be any type of force sensor, such as a piezo-resistive force sensor.

The device may be configured as a forceps or hemostat, that is, the shafts extend from the pivot axis opposite the integral jaw member to which it is attached, and the proximal portions of each shaft comprises a handle. The integral shafts may form a linear or substantially linear structure with the jaw member to which it is attached, as with Kelly forceps or a typical scissor. As such, the handle may comprise finger loops.

As described herein, the device may be attached by the conductors to one or more electronic or computer components for amplifying, monitoring, displaying, transmitting, converting, storing, and/or analyzing an electrical signal produced by the electronic force sensor, such as an amplifier.

Figure 1B:
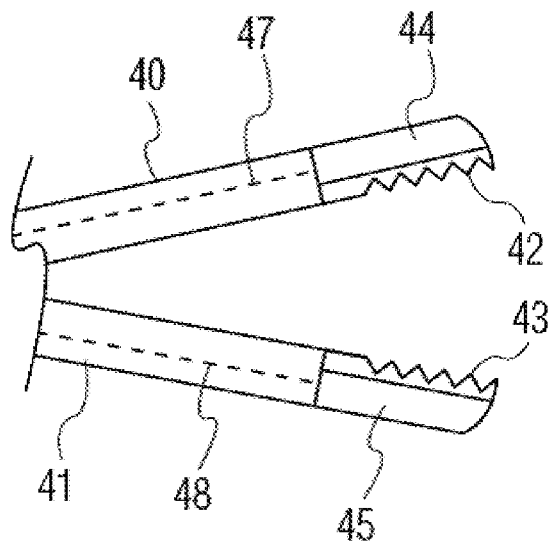
Figure 1C:
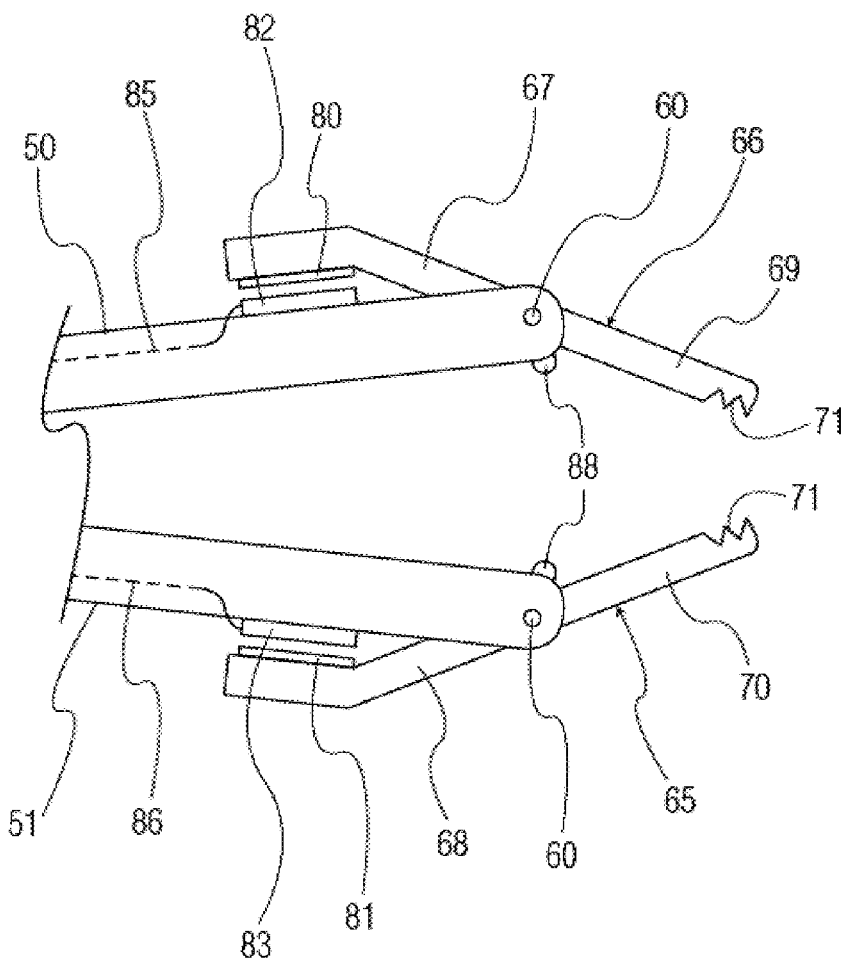

FIGS. 1A-C illustrate schematically various embodiments of the device, modeled after a traditional Kelly forceps or hemostat. As shown in FIG. 1A, the device 10 comprises two shafts 20 and 21 having proximal and distal portions, A and B, respectively. Shafts 20 and 21 are pivotally joined at pivot axis 22. The pivot axis 22 can be any useful structure, such as a pivot screw, rod, pin, rivet, bearings, etc., as are broadly known and understood in the mechanical arts. The shafts may be round ovoid, flattened, hollow, and, generally, of any useful length, shape, cross-sectional profile etc. Distal portion B also can be referred to as a jaw, comprising distal portions of the shafts and the pivot point. Handles 25 and 26 are shown at the proximal end, which may be finger or thumb holes, as are well-known in the art. A handle is a portion facilitating gripping of the device, e.g., by a surgeon. Optional latches are shown, which are shown as opposing teeth 27 and 28. At the distal end of shafts 20 and 21 are provided jaw members 40 and 41. As shown in FIG. 1B ("C" in FIG. 1A), jaw members 40 and 41 comprise inward-facing gripping surfaces 42 and 43, which may comprise grooves, teeth, roughened surfaces, cutting (ablative) surfaces etc. for gripping or otherwise manipulating, e.g., tissue, or bars, loops or hooks for manipulating sutures. A gripping surface refers to a surface that is intended to/configured to contact an object, tissue, etc., and may be any configuration, texture, etc., and can have an unmodified surface identical to the surface of the adjacent jaw members. Jaw members 40 and 41 also comprise electronic force sensors (shown schematically) which are configured to measure force applied by the jaw members 40 and 41 to, e.g., tissue. Jaw members comprise conductors (wires, shown in phantom) 47 and 48 for conducting electrical signals from the pressure sensors to external device(s) for monitoring, displaying, converting, amplifying (e.g., an inverting mode operational amplifier (OPAMP) with negative feedback, as shown below), storing, analyzing, transmitting, etc. the signal produced by the electronic force sensor. The conductors 47 and 48, as shown in FIGS. 1A and 1B may be affixed to shafts 20 or 21 or housed within a groove, or entirely within the shafts 20 or 21, and exit the device at any suitable point of egress which does not interfere with use/operation of the device, for instance, as is shown in FIG. 1A, in the proximal portion A. The conductor may terminate at a point on the device in a suitable plug or other electrical connector that can facilitate connection and disconnection of the device to suitable electronic components. In one embodiment, the device comprises only one force sensor, configured into one jaw member or the other.

FIG. 1C depicts an alternate embodiment of jaw members 40 and 41 of FIGS. 1A and 1B that can be used to measure inwardly-applied force (towards a median line between the jaws and applied by the device) or outward force (away from a median line between the jaws) applied to the device. Jaws 50 and 51 each comprise a pivot point 60 to which is attached arms 65 and 66, comprising proximal portions 67 and 68, respectively, and distal portions 69 and 70, respectively. Distal portions 69 and 70 comprise gripping surfaces 71, as outlined above. Proximal portions 67 and 68 comprise pads 80 and 81 on an inward-facing surface of arms 65 and 66, respectively. Pressure sensors 82 and 83 are connected to conductors 84 and 85 are shown attached to an outward-facing surface of jaw members 41 and 42. Stops 88 may be provided to prevent arms 65 and 66 from pivoting beyond a desired or useful angle with respect to the shafts. Stops 85 and 86 extend into pivot path of the arms to physically block movement of the arms past a certain point, and can be configured into the device in any suitable configuration, which is a matter of design choice and optimization. Pivot point(s) can be any useful pivot axis structure as described above, such as a rod, screw, rivet, pin, etc., as are broadly known in the mechanical arts.

In one embodiment (not shown) that is a common assembly method, protuberances are provided at the pivot point 60 on one or both of the arms 65 and 66 and corresponding holes or depressions are provided on or in the jaws 50 and 51 on surfaces facing the arms 65 and 66 and which engage the protuberances in a manner that attaches the arms 65 and 66 to the jaws 50 and 51 and permits the arms 65 and 66 to pivot about the pivot point 60. In assembling this embodiment of the device, the arms 65 and 66 can be snapped into place by forcing the protuberances into the corresponding holes or depressions. To facilitate assembly of the device, the protuberances can be spring-loaded pins that can be compressed until they are essentially flush with the surface of the jaws or arms into which they are assembled. In a similar embodiment, the arms 65 and 66 comprise the holes or depressions at their pivot points, and the protuberances are provided at pivot points on surfaces of the jaws 50 and 51 facing the arms 65 and 66.

Pads and pressure sensors may be configured in any useful orientation with respect to the arms and shafts, for example, with pads on the shaft and the pressure sensors on the arms. As indicated above, only one of the jaw members may be configured with a force sensor, and the jaw members may have different structures, such as a combination of a jaw member depicted in FIG. 1C and a jaw member configured as in FIG. 1B without the force sensor, akin to a typical jaw member of a hemostat.

Figure 1D:
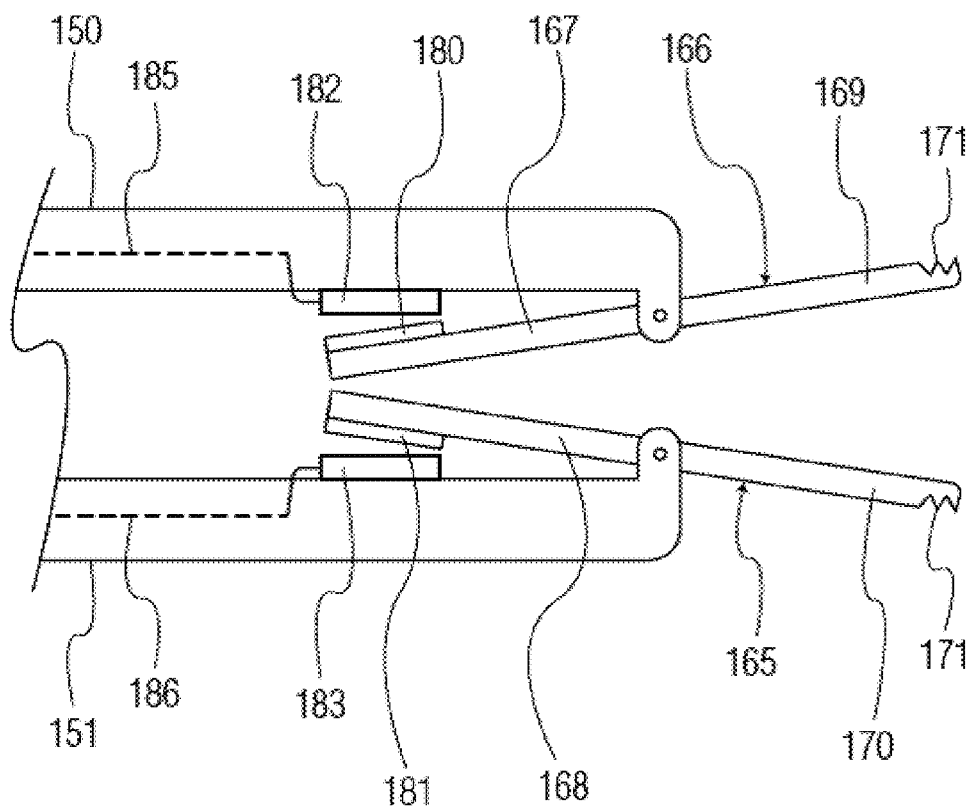

Referring to FIG. 1D, in a further embodiment of the devices shown in FIGS. 1A-1C, the gripping surfaces are located on an outward-facing surface of the jaw members and the force sensor is configured to measure force applied by the jaws in an outward direction or force applied to the device in an inward direction. Reference numbers 150, 151, 165-171, 180-183, 185 and 186 in FIG. 1D refer to like reference numbers and similar structures in FIG. 1C, though with a reversed orientation. Such a device would find use in opening a wound closure and measuring the force applied to a wound. In this variation on the device, the arms are inverted with respect to each jaw member as compared to the device depicted in FIG. 1C, so that the force sensors are on an inward-facing surface of the jaw members, the proximal portions of the arms and pads are then located between the jaw members (inward) and the gripping surface faces outward with respect to the device.

The terminal portion of the jaw members, for example as shown in the figures, may comprise gripping or grabbing elements, as a matter of design choice. The jaw members may comprises teeth, ridges, rough protuberances, hooks, bars, etc. in order to render the device useful for various purposes. One non-limiting example of such purposes is uses for which common forceps are used.

The handle or proximal portion of the device may also be configured in any useful manner. FIG. 1A shows a typical hemostat or Kelly forceps-type scissor-like configuration. Nevertheless, the force-sensing jaws can be configured into any type of forceps-like device with different handle configurations and mechanisms for closing the jaws, see, e.g., U.S. Pat. Nos. 5,209,747, 5,217,460, 7,083,620 and 7,708,757, incorporated herein by reference to the extent they disclose variations on the relationship between the jaw portions and jaw closing mechanisms for the jaws, or catheter devices.

Various types of force sensors are available, and their choice is a matter of design preference. Preferable force sensors are those that are sufficiently small so as not to interfere substantially with operation of the forceps, and capable of being repeatedly sterilized by, for instance, by exposure to ethanol or autoclaving. Because the device contains electrical components, autoclaving may not be an option unless the sensors and associated electronics can handle the autoclaving conditions without significant deterioration. One type of miniature pressure or force sensors are piezo-resistive pressure sensors, such as surface-mounted devices (SMD). Film force sensors (FLEXIFORCE®) are manufactured by Tekscan, Inc. of Boston Mass., with certain high-temperature models being able to withstand temperatures of up to 400° F.

Figure 2A:
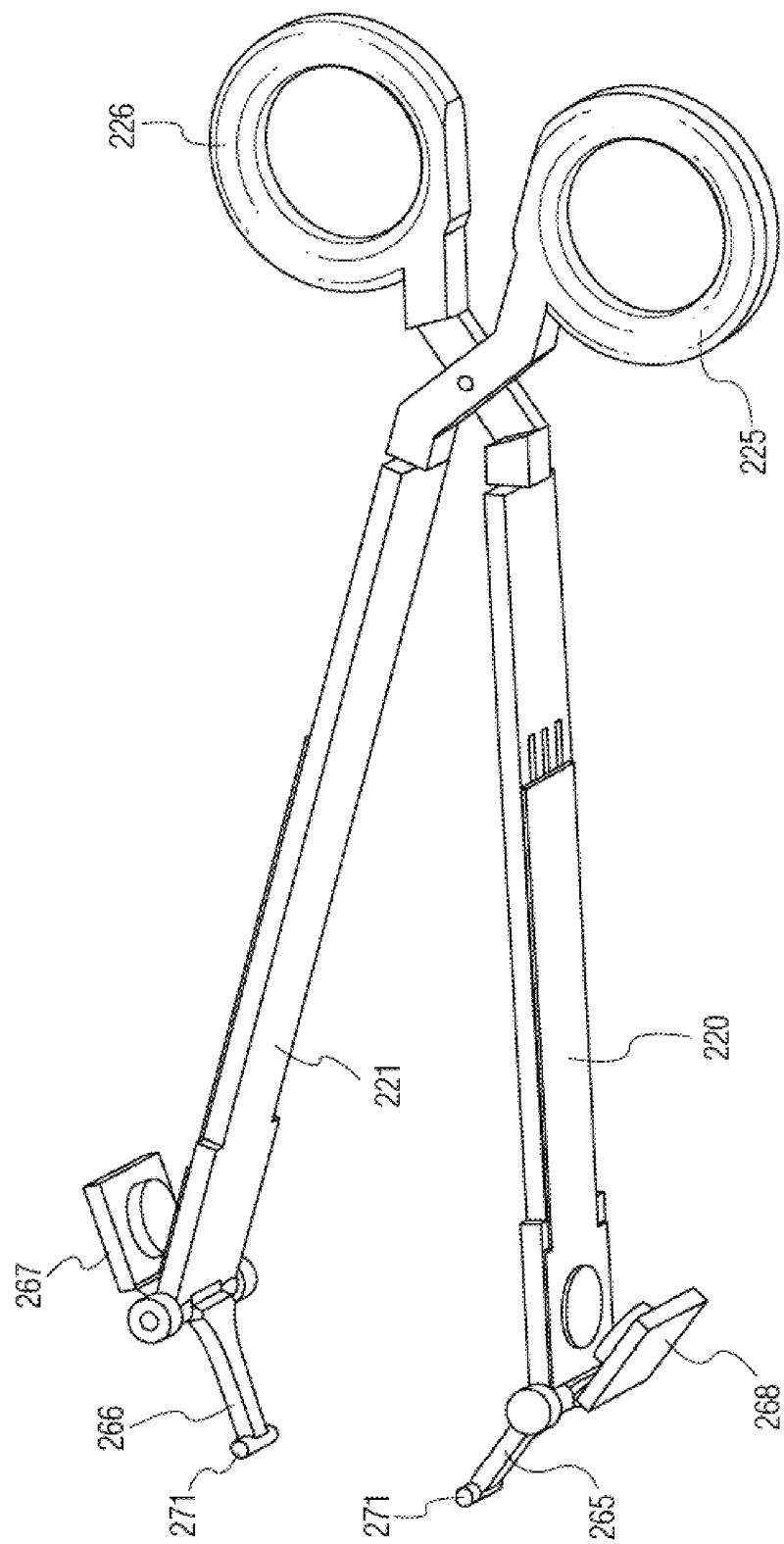
FIGS. 2A-D show schematically additional embodiments of the device described herein.
Figure 2B:
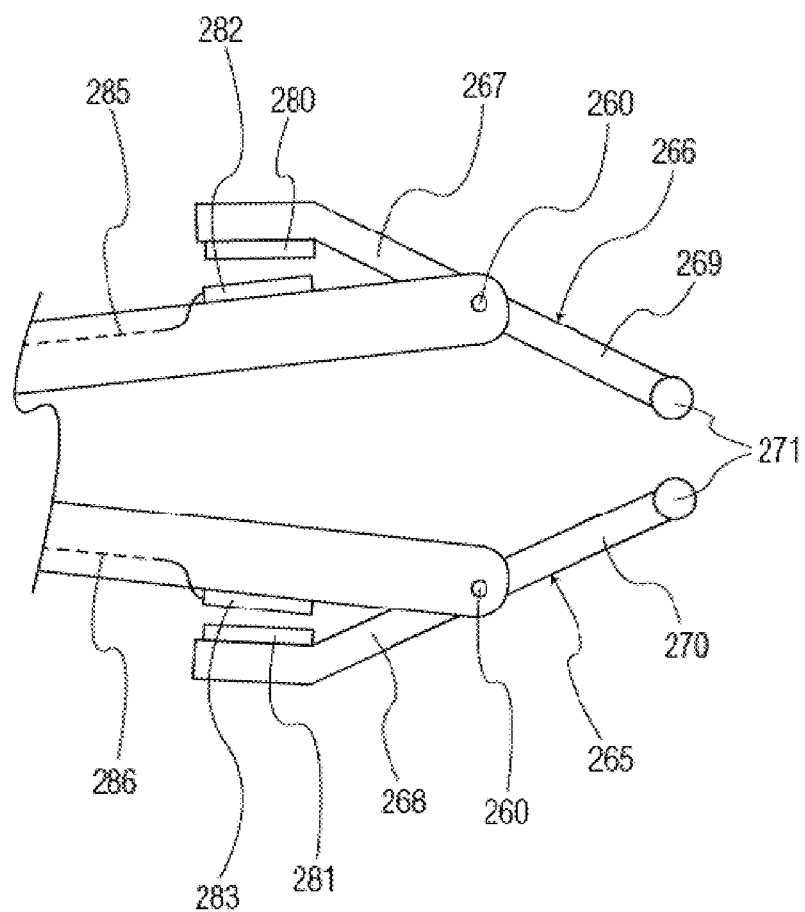
Figure 2C:
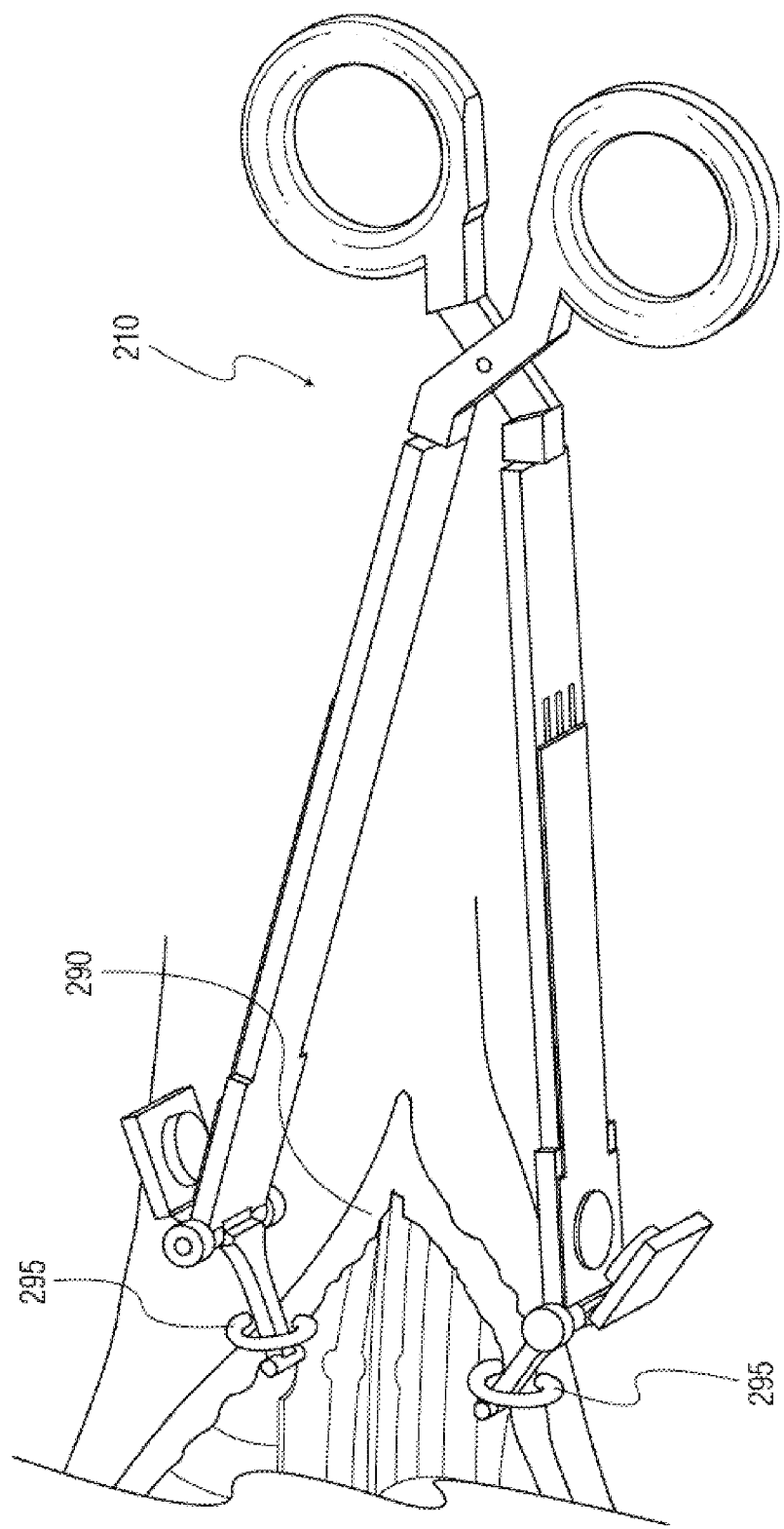
Figure 2D:
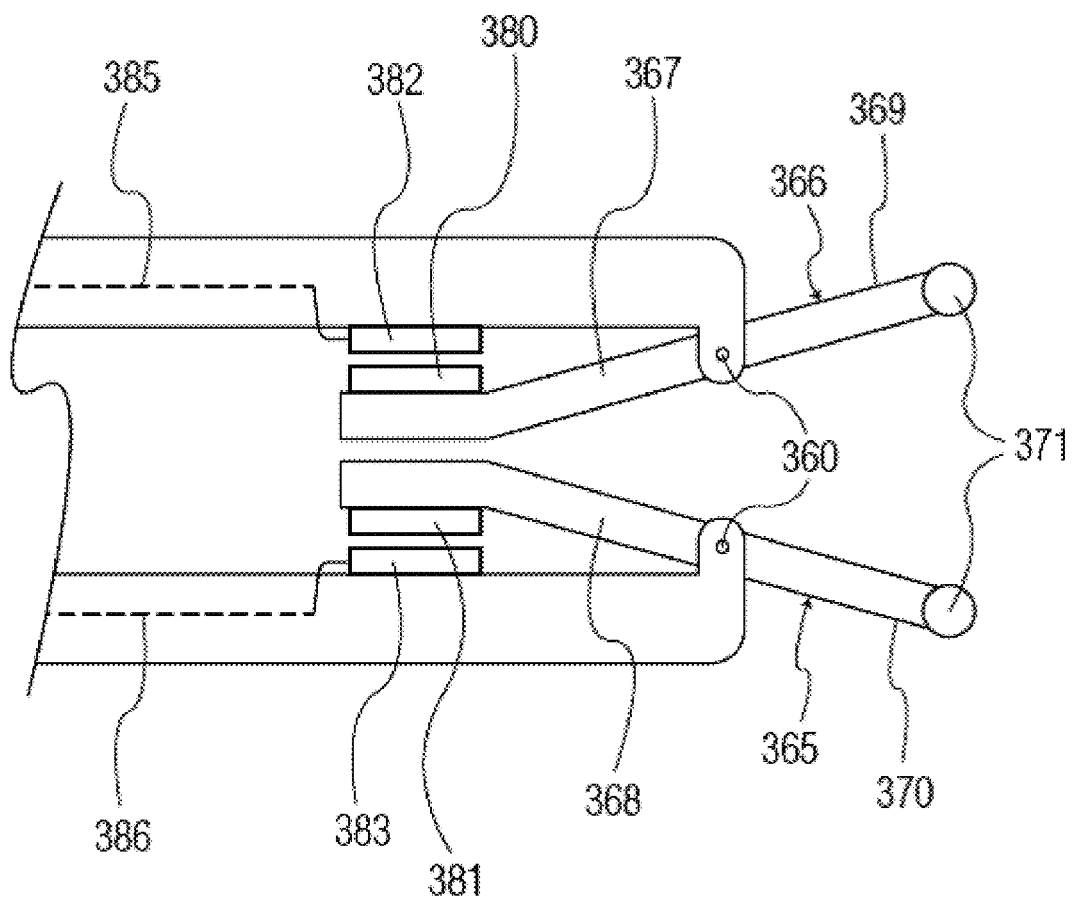

Alternate structures from those shown in FIGS. 1A-1D are shown in FIGS. 2A, 2B and 2D. FIG. 2A shows one embodiment of the device with bars as gripping surfaces that can be used to pull suture loops. FIGS. 2B and 2D shows schematics of distal portions of shafts similar to the embodiment described in reference to FIGS. 1C and 1D, respectively. FIG. 2C shows the device of FIGS. 2A and 2B in use closing a wound. In further detail, in reference to FIGS. 2A and 2B, a device 210 is provided that comprises two shafts 220 and 221 that are configured to pivot about a pivot axis. Handles 225 and 226 are provided. At a distal end of the device are arms 265 and 266 attached at pivot points 260 at distal ends of the shafts 220 and 221. The with proximal portions 267 and 268 of the arms 265 and 266 comprise pads, and distal portions 269 and 270 of the arms 265 and 266 comprise cross-bars 271. Pressure sensors 282 and 283 affixed to the shafts 220 and 221 and are connected to conductors 285 and 286. FIG. 2D shows a reverse embodiment of the device of FIGS. 2A and 2B, with like reference numbers 360, 365-371, 380-383, 385 and 385 referring to like structures in FIGS. 2A and 2B, but configured to measure inward, or outward-applied force. In the embodiments shown in FIGS. 2A-2D, the cross-bars are optionally grooved for increased grip.

Figure 3:
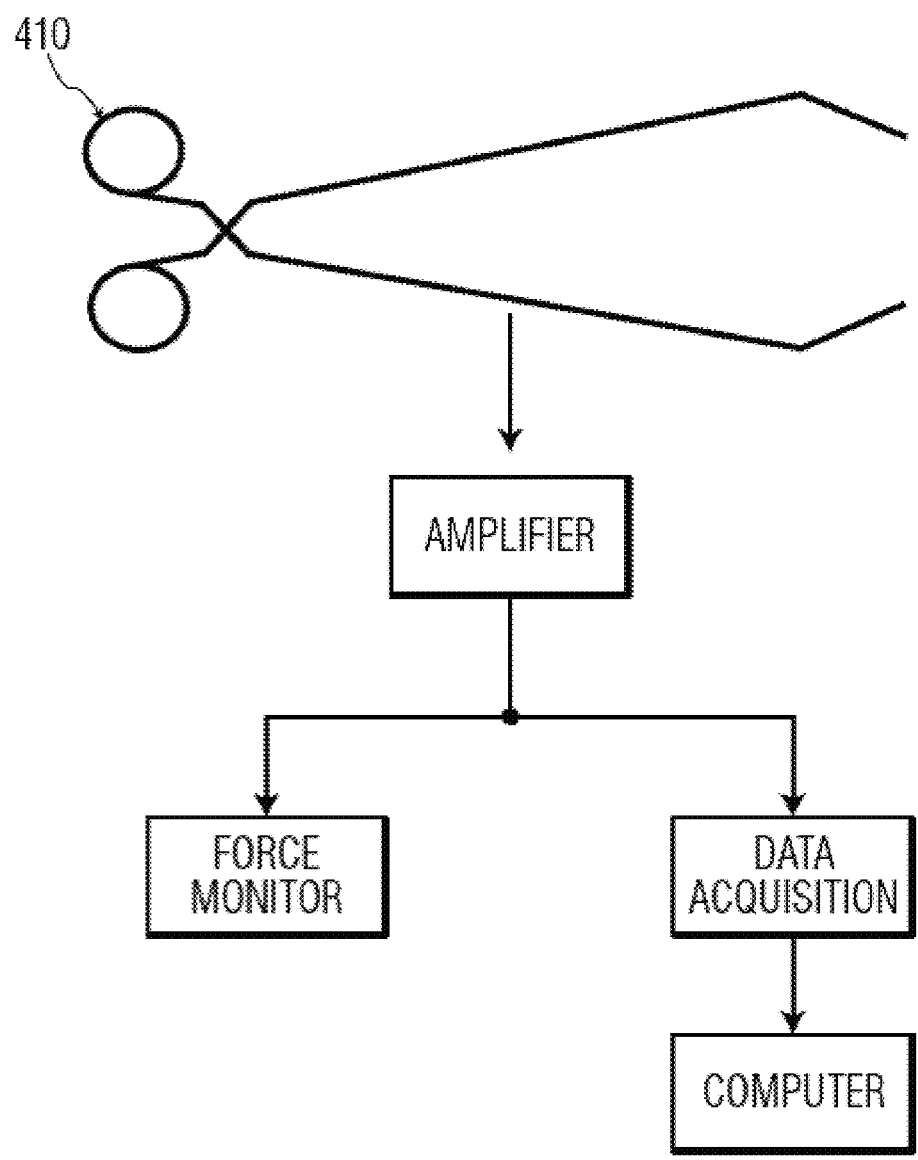
FIG. 3 is a flowchart depicting one embodiment of a tension measurement system as described herein. The output of the force sensor is amplified and displayed as force units in the monitor as well as continuously acquired and saved to a computer.
Figure 4:
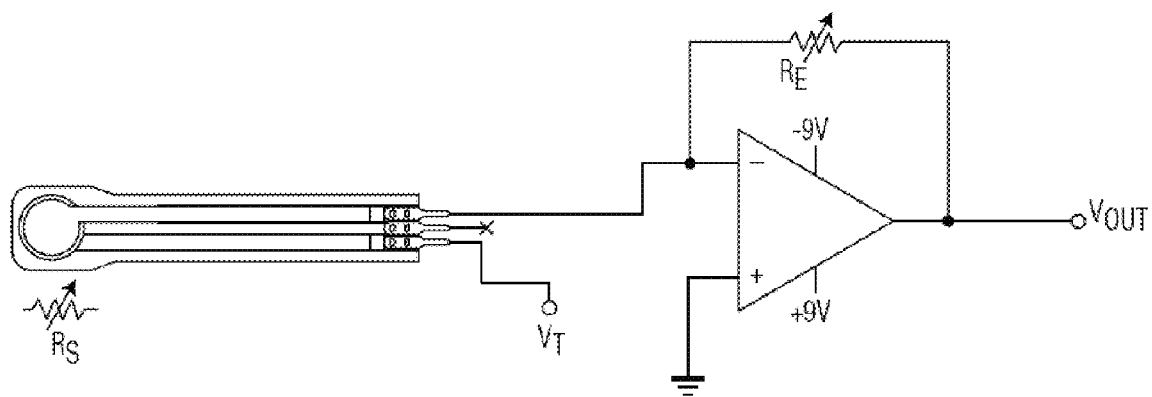
FIG. 4 is a schematic diagram of an amplifier circuit useful in connection with the devices described herein. A force sensing resistor Rs is connected in an inverting mode operational amplifier (OPAMP) with negative feedback and its relation to the output voltage $V_{out}$ is shown in the equation.

As shown in FIG. 3, a signal sent from the force sensor(s) of device 410 travels through conductors (wires, leads, etc.) to a device for amplifying the signal, which may be an op amp (shown in FIG. 4) or any useful amplifying electric circuit and/or electronics. The output of the device then can be displayed and/or recorded by any useful device as are widely known in the electronics and computer arts, such as an analog or digital gauge, or via a computing device, such as suitable software and/or hardware computer/computing processes ((e.g., programs or programming). Data obtained from the device also may be stored and optionally manipulated or converted in any useful form, encrypted or not, in electronic device memory or fixed media, including, without limitation RAM, ROM, Flash memory, SRAM, DRAM, magnetic tapes or discs, hard drives, optical discs, including CD, DVD, Blu-Ray, web-based or network-based data "clouds", etc. Any suitable computer or computing device, analog or digital, using any suitable operating system or electronic circuit configuration may be utilized to amplify, display, record, store and/or perform computations, and these activities may be divided among more than one device by wired or wireless methods. Computer processes, such as hardware and/or software operations or series of operations may be performed by any useful method, for instance by software programs and processes, such as spreadsheet and/or database programs. Useful computing devices include personal computers, servers, networks, mainframes, laptops, tablet PCs, PDAs, "smart" devices, cellular devices, etc. Additional information, such as ambient temperature, patient information, etc. also may be gathered and stored with the force data. Computers or computing devices include personal computers, PDAs (personal digital assistants), smart phones, etc., and their associated operating systems, algorithms, processes, software, hardware, etc.

In one embodiment, an alarm circuit or computer process is used in conjunction with the device measurement process, such that when a threshold force is reached a visual and/or audible signal is provided. Different signals or alarms may be used to signal different force intensities applied to or by the device. For example, when a first threshold is reached, a beep sounds, when a second threshold is reached, two beeps sound, etc. The same may be applied using lights, such as one or more LEDs incorporated in some manner into the device, such as incorporated into the handle of the device so that when an led lights up a specific force is applied. As with the audible signals, two or more "lights", such as LEDs may light up in sequence or at the same time when higher force thresholds are reached. These embodiments are readily implemented by one of ordinary skill in the art.

EXAMPLE

Figure 6:
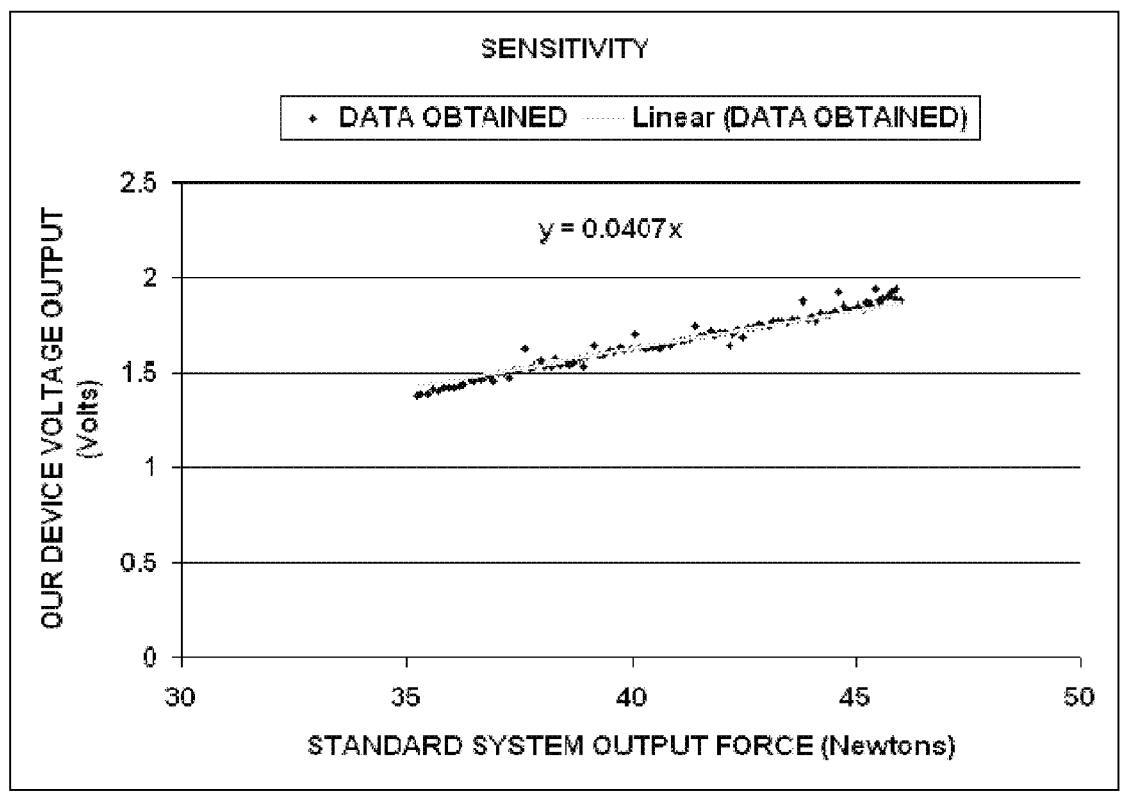
FIG. 6 shows the sensitivity of the device described in the example. The output voltage of the device was plotted against the force output of the standard system.

A surgical instrument was manufactured substantially as shown in FIGS. 2A and 2B. A schematic representation of the force measurement system with its different modules is shown in FIG. 3. An ultra-thin and highly sensitive force sensor was mounted onto an ergonomically comfortable forceps which can be sterilized using ETOH. The force sensor is a piezo-resistive sensing device in which the resistance is inversely proportional to the applied force. The swinging arm design of the instrument translates the tissue pulling force onto the force sensor. The force sensing resistor was embedded in an amplifier in such a way that the output voltage of the amplifier is inversely proportional to the resistance change in the force sensor as shown in FIG. 6. The amplifier voltage is calibrated into units of force and displayed on a monitor and simultaneously collected.

The design of this device is very rugged, compact, portable, and could be used for nearly any part of the body. The process of measuring the tension will also take minimal time. This is critical in surgery where lengthy measurement procedures can prove costly and unacceptable. Due to its simple design, the device will be easy to use and operable by one person. The simple design also allows the device to be built relatively inexpensively.

Figure 5:
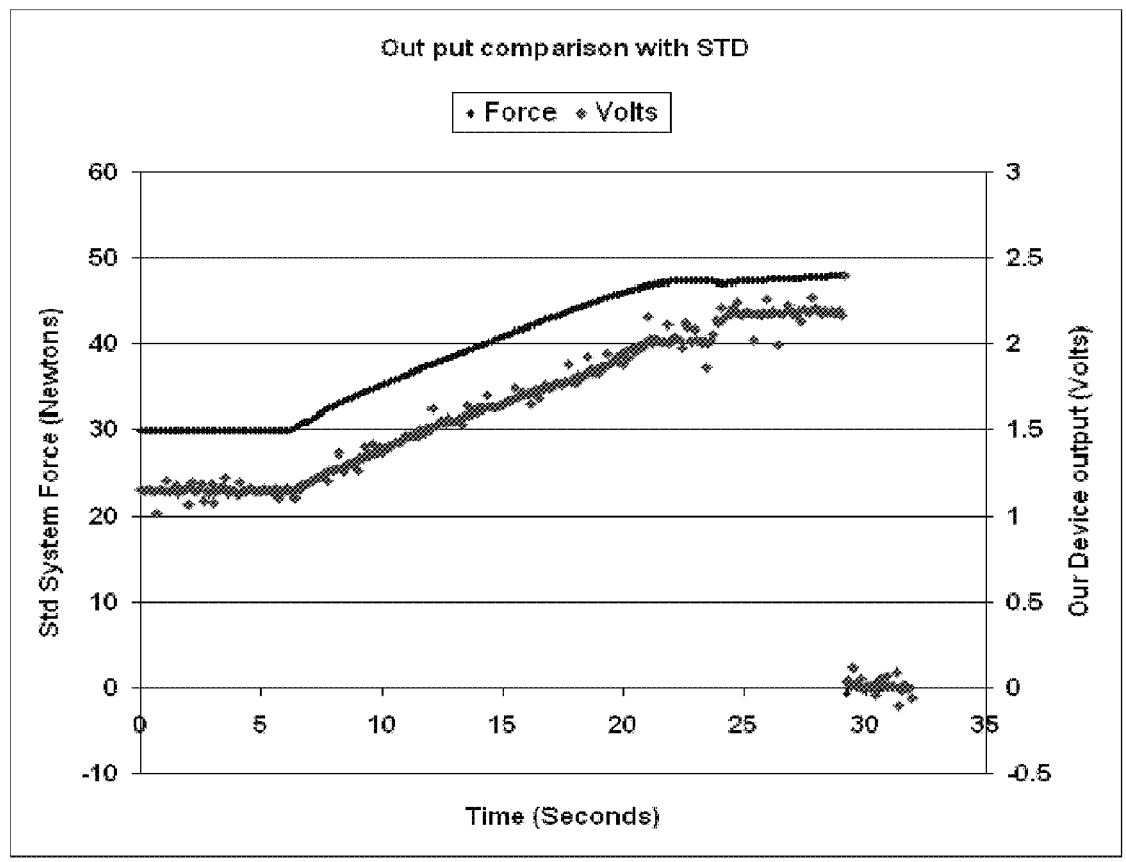
FIG. 5 shows the functionality of the device described in the example. The output data from the device in volts and force from an ASTM standard calibrated tensile testing system.

FIG. 5 shows the functionality of the device. The output data from the device in volts and force from an ASTM standard calibrated tensile testing system were acquired synchronously in a computer at the rate of 10 samples per second. When the device was pulled to the medial line after approx 6 seconds, the swinging arm translated the force applied on to the embedded force sensor leading to an increase in the voltage output of our device, which is corroborated by an increase in the force output of the standard system.

FIG. 6 shows the sensitivity of the device. The output voltage of the device was plotted against the force output of the standard system. The slope of the linear curve fit gives the sensitivity of the device, which was found to be 0.0407 Volts per Newton.

Figure 7:
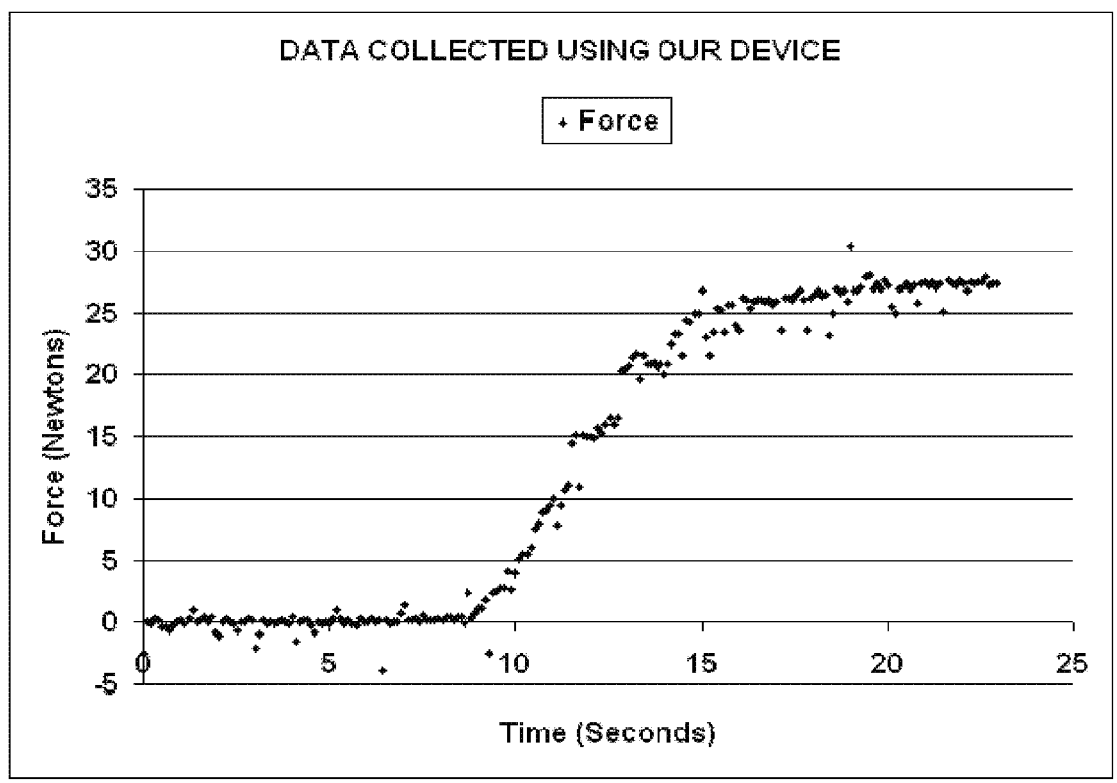
FIG. 7 shows representative data obtained using the device described in the example.

FIG. 7 shows representative data obtained using the device. Before pulling our device to the medial line, the base line of zero showed there was no force applied on the device. When the device was pulled, the swinging arm translates the force on the sensor and continues to grow as the force is further applied. The step increase in force data occurs when hemostat is locked in steps to the next level of lock.

Figure 8:
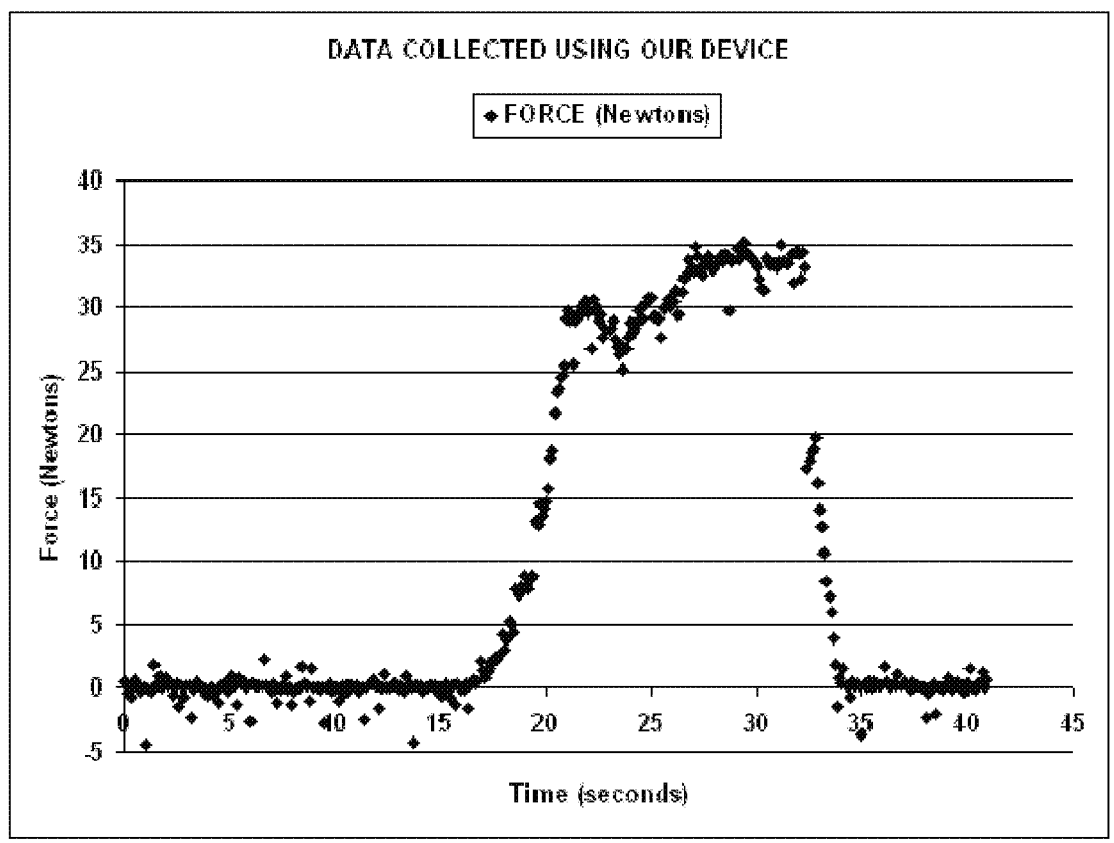
FIG. 8 shows representative data obtained using the device described in the example while closing in and moving away.

FIG. 8 shows representative data obtained using the device while closing in and moving away. The increase in force after 15 seconds occurs when the beams of forceps are pulled in towards medial line until all the locks of hemostat are locked completely. After holding the lock in place for 10 seconds they were released making the sensor embedded beams move away from the medial line. When these locks are released, a decrease in force was observed as the swinging arms were released.

Having described this invention above, it will be understood to those of ordinary skill in the art that the same can be performed within a wide and equivalent range of conditions, formulations and other parameters without affecting the scope of the invention or any embodiment thereof.

We claim:

1. A device, comprising;
a jaw comprising jaw members pivotally attached to each other at a pivot axis, the jaw members comprising a gripping surface distal to the pivot axis and one or both jaw members comprising an electronic force sensor configured to measure a force applied to the gripping surface;
levers mechanically linked to the jaws, each lever comprising a shaft integral with each jaw member and extending from the pivot axis, wherein the shafts extend from the pivot axis opposite the integral jaw member to which it is attached, and the proximal portions of each shaft comprising a handle; and
a conductor attached to the electronic force sensor.

2. The device of claim 1 in which the handle comprises finger loops.

3. The device of claim 1, in which the electronic force sensor is a piezo-resistive force sensor.

4. The device of claim 1 attached by the conductors to one or more electronic or computer components for amplifying, monitoring, displaying, transmitting, converting, storing, and/or analyzing an electrical signal produced by the electronic force sensor.

5. The device of claim 4 in which the conductors are connected to an amplifier.

6. A device, comprising;
a jaw comprising jaw members pivotally attached to each other at a pivot axis, the jaw members comprising a gripping surface distal to the pivot axis and one or both jaw members comprising an electronic force sensor configured to measure a force applied to the gripping surface;
levers mechanically linked to the jaws, each lever comprising a shaft integral with each jaw member and extending from the pivot axis; and
a conductor attached to the electronic force sensor, wherein either:
a) one or both of the jaw members comprises a first portion attached to the other jaw member at the pivot axis, the first portion having an inward-facing and an outward-facing surface, a distal end, a force sensor on the outward facing surface of the first portion, and an arm having a proximal and distal portion and pivotally attached to the distal end of the first portion at a second pivot axis between the proximal and distal portions of the arm, the distal portion of the arm extending beyond the distal end of the first portion and comprising the gripping surface, the proximal portion of the arm extending over the force sensor and which engages the electronic force sensor when force is applied to an inward-facing side of the gripping surface causing the arm to pivot about the second pivot axis; or
b) one or both of the jaw members comprises a first portion attached to the other jaw member at the pivot axis, the first portion having an inward-facing and an outward-facing surface, a distal end, a force sensor on the inward facing surface of the first portion, and an arm having a proximal and distal portion and pivotally attached at a second pivot axis between the proximal and distal portions of the arm, the distal portion of the arm extending beyond the distal end of the first portion and comprising the gripping surface, the proximal portion of the arm extending over the force sensor and which engages the electronic force sensor when force is applied to an outward-facing side of the gripping surface causing the arm to pivot about the second pivot axis.

7. The device of claim 6, in which the electronic force sensor is a piezo-resistive force sensor.

8. The device of claim 6 attached by the conductors to one or more electronic or computer components for amplifying, monitoring, displaying, transmitting, converting, storing, and/or analyzing an electrical signal produced by the electronic force sensor.

9. The device of claim 8 in which the conductors are connected to an amplifier.

10. The device of claim 6, each lever comprising a shaft integral with each jaw members and extending from the pivot axis.

11. The device of claim 10, in which the shafts extend from the pivot axis opposite the integral jaw member to which it is attached, and the proximal portions of each shaft comprising a handle.

12. The device of claim 11, in which the handle comprises finger loops.

13. The device of claim 6, wherein one or both of the jaw members comprises a first portion attached to the other jaw member at the pivot axis, the first portion having an inward-facing and an outward-facing surface, a distal end, a force sensor on the outward facing surface of the first portion, and an arm having a proximal and distal portion and pivotally attached to the distal end of the first portion at a second pivot axis between the proximal and distal portions of the arm, the distal portion of the arm extending beyond the distal end of the first portion and comprising the gripping surface, the proximal portion of the arm extending over the force sensor and which engages the electronic force sensor when force is applied to an inward-facing side of the gripping surface causing the arm to pivot about the second pivot axis.

14. The device of claim 6, wherein one or both of the jaw members comprises a first portion attached to the other jaw member at the pivot axis, the first portion having an inward-facing and an outward-facing surface, a distal end, a force sensor on the inward facing surface of the first portion, and an arm having a proximal and distal portion and pivotally attached at a second pivot axis between the proximal and distal portions of the arm, the distal portion of the arm extending beyond the distal end of the first portion and comprising the gripping surface, the proximal portion of the arm extending over the force sensor and which engages the electronic force sensor when force is applied to an outward-facing side of the gripping surface causing the arm to pivot about the second pivot axis.

15. The device of claim 6 in which the arms pivot in substantially the same plane as the distal end of the jaw members.

16. The device of claim 6, in which a surface of the proximal portion of the arm facing the electronic force sensor comprises a protuberance aligned to engage the force sensor.

17. The device of claim 6, in which one of the arms or the shafts comprise one or more stops for limiting movement of the arm about the pivot axis.

* * * * *